United States Patent [19]
Bukamier et al.

[11] 4,333,812
[45] Jun. 8, 1982

[54] ORIENTATION-INSENSITIVE ELECTRODE

[76] Inventors: Gary L. Bukamier, 4358 E. La Palma, Anaheim, Calif. 92807; Steven L. Rupert, 600 Langsdorf Dr., Fullerton, Calif. 92631

[21] Appl. No.: 163,710

[22] Filed: Jun. 27, 1980

[51] Int. Cl.³ .................. G01N 27/30; G01N 27/36
[52] U.S. Cl. ..................... 204/195 G; 204/195 M; 204/195 L
[58] Field of Search .......... 204/195 G, 195 F, 195 M, 204/195 L, 195 B, 195 R; 128/635

[56] References Cited
U.S. PATENT DOCUMENTS 3,188,285  6/1965  Watanabe et al. ............. 204/195 G
3,551,315 12/1970  Friconneau et al. ........... 204/195 G
3,930,976  1/1976  Owen ........................... 204/195 G
4,012,308  3/1977  Jerrold-Jones et al. ....... 204/195 F Primary Examiner—G. L. Kaplan

[57] ABSTRACT

Included in the body of ion sensitive and selective electrodes and reference electrodes is a plug which engages the electrolyte and yields and reforms with expansion and contraction of the electrolyte body. The plug maintains pressure on the electrolyte eliminating air and preventing the formation of bubbles. The result is an electrode which is useful in any spacial orientation and which has an extended upper limit temperature operating range.

9 Claims, 7 Drawing Figures

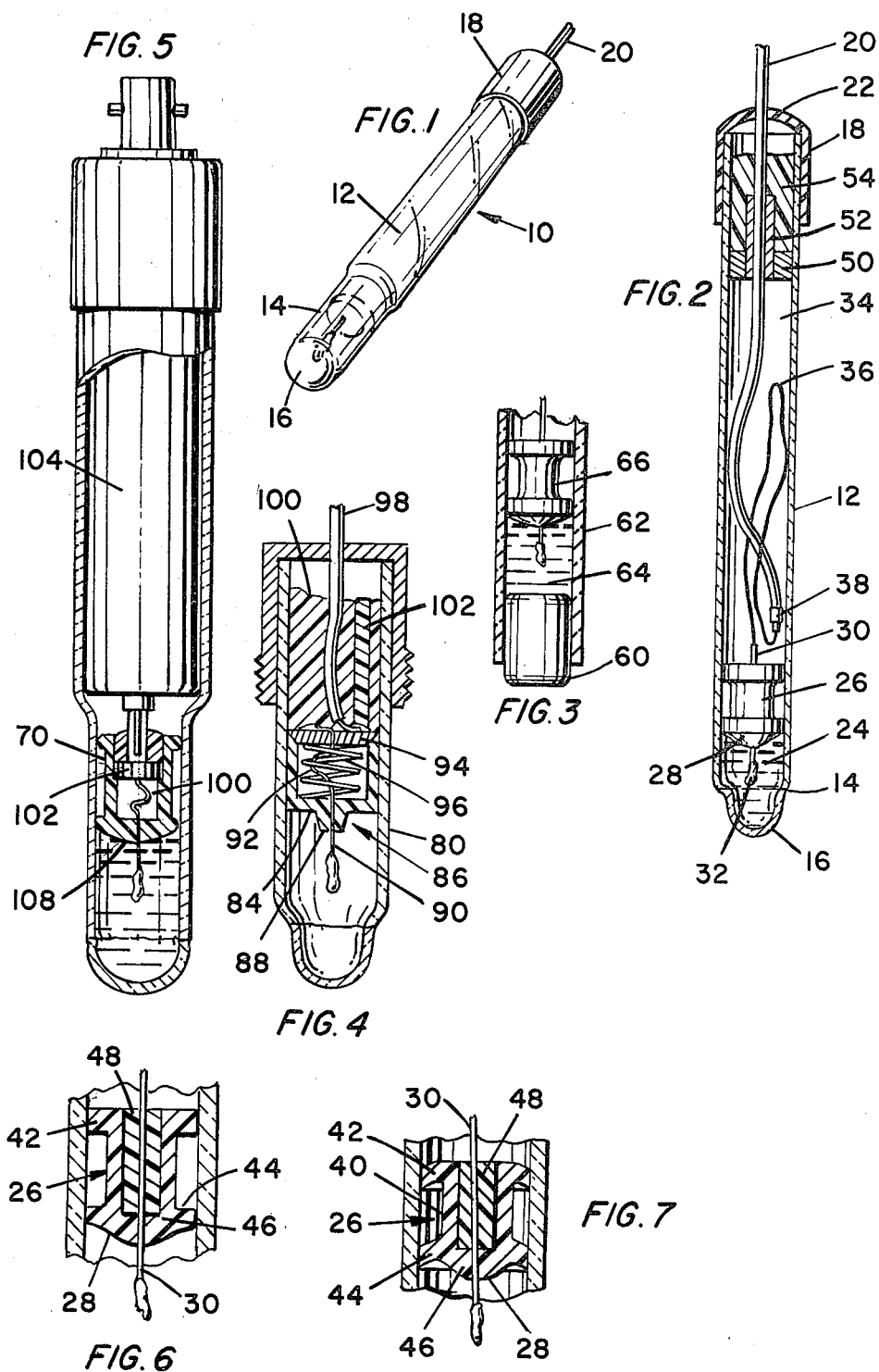

ORIENTATION-INSENSITIVE ELECTRODE

TECHNICAL FIELD

This invention relates to improvements in the structure and the manner of sealing the electrolyte in ion selective electrodes and reference half cells.

BACKGROUND OF THE INVENTION

In the fields of chemical processing, food preparation, waste treatment, health services, and many others, it is common to employ electro-chemical techniques to detect the presence or to determine the concentration of particular chemicals. Electro-chemical measurement is complicated by the fact that signal levels are very low, and complicated by the further fact that available sensors exhibit high impedance. In most cases it is necessary to include a liquid path in the measuring circuit to permit ion migration. The structure of the sensor is required to have high impedance and to be inert. These factors and others, including the fact that a glass membrane is used in the most common application, the sensing of pH, and the use of universal read-out instrumentation and sensor mounting structures, have led to a high degree of standardization in the configuration of ion selective electrode sensors and reference electrodes.

Most electrodes are formed as elongated cylinders in which the ion selective element, or the salt bridge in the case of a reference electrode, are located at one end of the cylinder. The electrical leads or the electrical connectors are located at the cylinder's opposite end. The most commonly used material for forming the cylindrical body is tubular glass. Glass is inert, and it bonds readily to pH sensitive glass. Even when plastics, the other popular body material, is used, the body is usually formed as an elongated cylinder.

That portion of the electrical measurement path in which ion movement occurs must form a junction with the sensor, hence it is almost universal that the liquid be contained within the tubular electrode body. The liquid is conductive, an electrolyte, and it is made conductive by the addition of a salt. To simplify correction of the result to account for junction potentials, the salt is added to saturation and connection to the liquid is made through a chemically related material. Commonly, the electrolyte is a saturated solution of KCl, and connection to the instrumentation is made through a silver wire coated with silver and silver chloride. The electrode must include a closure because it is a liquid container, and in almost all cases the instrument wire is the center conductor of a coaxial cable that extends through the closure.

What has been set out above is a description of the structural form that is produced by almost all of the manufacturers in this field which has enjoyed the greatest commercial success for the longest period, and which has long been the subject of cost reduction and performance improvement inventive effort. Despite past efforts, though, this standard, cost reduced, high performance electrode form has a severe limitation. It cannot be used upside down (selective end up) in many installations. Air bubbles in the electrolyte interrupt, or change the area of, the ion migration portion of the measurement current flow path. The obvious solution is to completely fill in the electrolyte cavity, but that does not solve the problem. During the course of manufacture, shipment and use, the electrolyte experiences a wide range of temperatures. Those temperatures may range from below zero degrees centigrade (freezing) to above 100 degrees centigrade (boiling). The electrolyte is incompressible and it undergoes relatively large changes in volume. It is part of the standard design to include an air bubble whereby to accommodate volumetric change.

SUMMARY OF THE INVENTION

It is an object of this invention to eliminate the air bubble in the electrolyte. It is an object to provide an electrode which exhibits the same performance characteristics in any special orientation.

Another object is to extend the upper temperature limit at which liquid electrolyte sensors and reference electrodes may be used.

A further object is to provide the advantages of insensitivity to orientation and increased temperature range in the conventional sensor body forms.

The invention is not limited in that sense. It is applicable to a wide variety of enclosure and body shapes and sizes and forms, but one of its advantages is that it can be incorporated in existing forms with minimum obsolesence of existing technology.

These several advantages, and others that will be apparent upon a reading of the specification that follows, are realized in part by the provision in an electrode of the kind in which a container for electrolyte includes a wall at which electro-chemical sensing is to be accomplished, and the inclusion of a body of electrolyte disposed in said container overlying said wall, maintaining means for maintaining said electrolyte in intimate contact with said wall against gravitational force in every spacial orientation of the electrode, said maintaining means comprising a structure which is trapped between said container and said body of electrolyte and which yields to permit the volume of said electrolyte to increase with temperature and which is biased to maintain intimate contact with said electrolyte to prevent formation of bubbles as the volume of electrolyte is decreased.

When, as in most cases, the electrode body includes a cylindrical inner wall, the preferred kind of "maintaining means" is a plug in the form of a diaphragm or piston, or something between them. Each of these forms provides specific advantages.

Whatever the form, it is a feature to provide a gas space in which gas (usually air) is compressed and reexpanded to accommodate changes in electrolyte volume. That function can be provided using a resilient element which may be separate or can be incorporated by making the plug of resilient material.

It is also a feature to employ an air or gas filled cavity as part of the plug structure whereby to create a seal against leakage of electrolyte past the plug. That feature is advantageously employed when the electrode body is made of glass or plastic and has a relatively smooth inner wall. In one refinement of the invention, the air in the cavity is heated with heating of the electrolyte to increase air or gas pressure and tighten the seal.

Additional features and advantages of the invention will be understood from the drawings and detailed description of the preferred forms of the invention.

THE DRAWINGS

In the drawings:

FIG. 1 is an isometric view of a pH sensor electrode in which the invention is embodied;

FIG. 2 is a view in central vertical section of the electrode of FIG. 1;

FIG. 3 is a view in central vertical section of the salt bridge end of a reference electrode in which the invention is embodied;

FIG. 4 is a view in central vertical section of an alternate form of the invention embodied in a pH sensor electrode;

FIG. 5 is a view partly in elevation and partly in central vertical section of a pH sensor electrode in which still another form of the invention is embodied, the electronic package being depicted symbolically;

FIG. 6 is a view in central vertical section of the elements that form the electrolyte retaining means of FIGS. 1 and 2 shown in the condition that characterizes them when the electrolyte is cold and occupies minimum volume; and FIG. 7 is a cross-sectional view showing the elements of FIG. 6 in the condition that obtains when the electrolyte is at near maximum allowable temperature and volume.

DESCRIPTION OF THE PREFERRED EMBODIMENT

FIG. 1 is an isometric view of a low cost, high performance pH sensor electrode 10 the external elements of which have common standard form. The body 12 is a length of 8 mm outside diameter glass tubing. At its sensor end 14 the tube has been reshaped to slightly smaller diameter. That end was heated and dipped into a body of molten pH sensitive glass. The glob of glass that adhered to the tube on being withdrawn was blown into the bulbous end 16.

At its opposite end a cap 18 is fitted on the end of the tube and a length of coaxial cable 20 extends from the cap. This electrode is 8 mm in diameter over most of its thirteen centimeter plus length which is a popular standard size.

The interior of the sensor may be seen in FIG. 2. The cap 18, here shown in section, is cup-shaped. The cup is shown inverted. Its side walls have inside diameter to make a sliding fit over the end of the glass tube. The cup walls are bonded to the glass wall by an adhesive layer so thin that it is not visible in the drawing.

At the sensor end of the electrode, the pH sensitive glass bulb 16 is generally semi-hemispherical. It is bonded at its equator to the lower end 14 of glass tube 12. A body 24 of electrolyte is contained within the bulb 16 and the lower end of the tube. A plug 26 extends across the cross-sectional area of the tube. One end face, the lower face 28 in FIG. 2, contacts the upper surface of the electrolyte body. It is in intimate contact with the liquid and is forced against the liquid such that no air is present in the electrode in the space below the plug 26. The pressure on the liquid is maintained such that no bubbles are formed in the electrolyte even at temperatures above 100 degrees centigrade. The electrolyte in this case is a solution of KCl.

Electrical contact is made with the electrolyte through a silver wire 30 and the silver-silver chloride coating 32 which is bonded to the electrolyte end of wire 30 by any suitable means such as by sintering. The wire extends entirely through the plug to the air space 34 where it is soldered or otherwise bonded to a length 36 of unshielded lead wire. The other end of the lead wire is soldered to the center conductor at the end 38 of coaxial cable 20. The shield braid of the cable is cut off and left unconnected.

The function of the braid is to shield the current carrying inner conductor from stray magnetic and electrical fields that might induce false potentials across lengths of the conductor. To prevent that, the end of the coaxial cable and its shield braid are brought to the lowest possible point in the tube. That point, in this embodiment, is adjacent the plug 26. That function is not disturbed by the addition of the extension wire 36. That wire is included for convenience. It is attached to silver wire 30 after wire 30 is assembled with plug 26 and before the plug is inserted into the tube. The extension wire is made sufficiently long so that it extends to a point outside the tube where it is readily soldered to the coaxial cable conductor. When the end of the cable is inserted down into the tube, the extension wire 36 is doubled back on itself. Any potential that is induced in the upwardly extending portion of the wire 36 is cancelled by a corresponding potential induced in the downwardly extending portion. Because the coaxial cable extends only in one direction, potentials induced in its conductor are not cancelled whereby it needs to be shielded.

The cable could be soldered to silver wire 30 prior to insertion of the plug into the tube, but the manner of plug insertion makes that less convenient.

The plug 26 is made of a resilient material. It is symmetrical about its longitudinal axis so its shape is defined by the cross-sectional views in FIGS. 6 and 7. In both cases, the section is taken on a plane that contains the axis. The same plug 26 is shown in FIGS. 1, 2, 6 and 7. FIG. 7 shows how the plug is deformed in response to an increase in pressure at its forward face 28 relative to its opposite face.

The plug can be described as being cup-shaped except that outwardly extending flanges are formed on the cup at the upper and lower ends of the cup wall. For identification, the cup is designated 40. The upper flange 42, at the upper rim of the cup wall, and the lower flange 44 are integrally formed with the cup. The inner wall of the cup bottom 46 lies in a plane that is perpendicular to the plug axis. The outer face 28 is somewhat conical. The apex extends downwardly. Thus, the cup bottom is thicker at its central axis. The silver wire 30 extends through a hole that is pierced through the bottom wall and it is gripped by the resilient material surrounding the hole. Because the cup wall is thicker at its axis, that gripping action occurs over a longer region of the wire. That feature is important when the cup interior is made an air cavity because it results in the wire being held more tightly. In this embodiment, the cup is filled with a body 48 of resilient polymeric material which bonds to the wire and to the cup, and the gripping force at the cup bottom is less important. However, the conical shape at the lower face 28 is preferred for another reason. The conical shape facilitates removal of all air from the electrolyte cavity below the plug.

Prior to insertion of the wire into the tube, the lower end is coated with a paste containing metallic silver and silver chloride. The paste is heated to drive off the binder material and to bond the silver-silver chloride coating 32 to the wire. Next, the wire is inserted through the cup bottom. The cup is filled with the resin body 48 and an end of the extension wire is soldered to the upper end of the silver wire. The next steps are to add the electrolyte to the tube and to insert the plug assembly.

A number of different techniques can be employed, but the preferred technique is to insert a relatively thin assembly wire into the tubular glass body 12 from its upper end to a point adjacent the lower end 14 of the tube. The tube is held end 14 down while a measured quantity of KCl and a small additional quantity of KCl are placed in the tube. Then the plug assembly is inserted and is forced downwardly along the wire and the inner wall of the tube down into contact with the electrolyte.

The flanges 42 and 44 have a diameter, in relaxed condition, which is larger than the inside diameter of the tube 12. Being resilient, the flanges will deform to smaller diameter whereby the plug can be forced into the tube. Additional deformation occurs at the points at which the flanges engage the assembly wire. The diameter of the wire is selected so that the deformation creates a flow path for the escape of air as the plug is forced downwardly toward the body of electrolyte. When the plug engages the upper face of the body of liquid electrolyte, the apex of face 28 enters into the liquid and air is forced toward the margins. Tipping the assembly insures that any remaining air is driven past the assembly wire. Downward force is discontinued when all air has been removed from the electrolyte space. The assembly wire is withdrawn and the structure has the shape depicted in FIG. 6. The annular space around the body of the cup and between flanges 42 and 44 is filled with air. If a small amount of electrolyte has been forced into this space, no harm will have been done.

It should be mentioned that in special applications it may be necessary or desirable that the air space around and above the plug be filled with a gas other than air, and that can be accomplished by conducting the assembly process in an enclosure which has been filled with that gas.

The assembly of the electrode of FIGS. 1 and 2 is completed by threading the cable 20 through the sleeve 50 and flange 52 combination, and sliding the sleeve and flange into the glass tube 12 to a point at which the upper end of the sleeve is below the upper rim of the tube. The space above the flange is filled with a rapidly hardening adhesive resin which hardens to form a plug or seal 54 against the passage of air into or out of the tube below the seal. The function of the sleeve and flange is to position the coaxial cable centrally in the tube and to define the lower end of the sealing plug.

When the electrode and its electrolyte are heated, the electrolyte is expanded to greater volume. The amount of that expansion is small because the body of electrolyte is small. The expansion is easily accommodated by deformation of the plug to a shape similar to what is depicted in FIG. 7. In this embodiment, the flanges 42 and 44 yield and the central portion of the plug, the cup portion and the filler 48, are moved rearwardly in a piston action. The renitance of the flange material returns the plug to the condition depicted in FIG. 6 when electrolyte temperature and volume are reduced.

The increase in pressure on the plug, as an incident to increase in electrolyte volume, tends to force the plug upwardly in the tube. When the electrolyte temperature and volume are reduced the pressure of the air in the space between the plug and flange 50 tend to force the plug downwardly. The inner surfaces of glass tubes and the outer surfaces of plastic or synthetic rubber plugs have a relatively low coefficient of friction so that slight motions of the plug might occur when temperature excursions are great and especially when changes occur cyclically and rapidly. Even if plug movement occurs, the function of the sensor is not disturbed. However, the plug 26 is designed to prevent plug position change. The pressure of the air in the annular space between the plug flanges is increased as electrolyte temperature is increased because the heat flow path across the plug flange 44 from face 28 to the air space is short and because the plug material is selected to be a relatively good heat conductor. The air in that space expands and applies increased pressure to the flanges. The effect is to increase the force with which the flanges bear against the tube wall and translation of the plug is prevented.

The end result is an effective, low cost electrode that can be mounted in any position. The silver wire is shorter and, therefore, less costly than it is in conventional designs. Except for the slight reduction at end 14, the glass tube is a standard, high volume, low cost element. The slight necking is accomplished to insure that the diameter of the sensor bulb is not greater than the tube diameter. The degree of diameter reduction is not critical. It can be reduced at the time the end is heated in preparation for adding the glob of pH sensitive glass. The glob is added in a dipping step after which the blower blows the bulb. The process is simple and less expensive by far than the cost of producing the standard double wall electrode bodies.

The plug assembly can be manufactured separately and in advance of the other elements so that there is no need to interrupt manufacture to await curing of the filler material 48. The only curing that is required during assembly is curing of the stopper material 54. The effect of that is to make automatic assembly feasible, especially because curing can proceed after the cup 18 has been added. The adhesive by which the cup is attached to the glass can be dried while the polymeric body 54 is hardening. Thus it is that the assembly process is very simple and inexpensive.

But the advantage of the invention is not limited to ease of manufacture. The invention provides improved performance at high temperature. The upper limit of sensor performance in the case of most sensors is 105 degrees centigrade, or less. In this sensor, the absence of air in the electrolyte space results in an increase in the boiling temperature. The sensor of FIGS. 1 and 2 may be operated at temperatures up to 150 degrees centigrade. Further, the electrode may be operated in any spacial orientation from bulb down to bulb up without any change in calibration or in performance characteristics.

In the embodiment of FIGS. 1 and 2, the central portion of the plug was made to operate with a piston action. If the filler material 48 is omitted, or if the cup is only partially filled to create a sealed air cavity, as shown in the plug 70 of FIG. 5, then the bottom of the cup can move more readily. It behaves like a diaphragm. The diaphragm action accommodates electrolyte volume change more readily. To do that sacrifices some of the increase in upper limit temperature range, but it makes the invention applicable to ion selective electrodes and reference electrodes which rely on salt bridges and the various kinds of membranes that permit ion migration between the test solution and the electrolyte.

Such an electrode is shown in FIG. 3. A cylinder 60 of porous material is cemented into the end of a plastic, tubular, electrode body. The porous cylinder is wetted with electrolyte and sample liquid to form liquid paths across the cylinder in which ion migration can occur.

The inclusion of substances which oppose migration of certain ions or promote migration of certain ions makes the cylinder or "membrane" ion selective or ion sensitive.

Unless some other means is provided for accommodating volumetric change in the electrolyte body 64, change results in forcing electrolyte into the membrane and then drawing it back into the electrolyte cavity. The conventional design minimizes that effect by including a body of air in the electrolyte cavity. The air, being compressible, serves as an accumulator or spring in which expansion is accommodated when the electrolyte is heated. But the inclusion of air limits the orientation of the electrode. The provision of an ion selective or ion sensitive electrode that can be operated sensor up may not be much value if the reference electrode cannot be operated with the salt bridge up. Installation of the plug 66 in the reference electrode, such that all air and air bubbles are eliminated from the electrolyte cavity, permits bridge end up operation. Making the plug pliable so that volumetric change is readily accommodated minimizes the degree in which temperature change causes electrolyte flow in the bridge 60.

In this case, the plug 60 is just like the plug 26 of the earlier described embodiment, except for the omission of any filler from the interior of the cup. The silver wire 68 and its silver-silver chloride coating are just like wire 30 and coating 32 of FIGS. 2, 6 and 7.

The electrode shown in FIG. 4 is a pH sensor. Its glass body 80 is fitted with a pH sensitive glass bulb 82. The bulb and the lower part of the body are filled with a quantity of saturated electrolyte up to the lower face 84 of the cup-shaped plug 86. The plug is formed of a resilient material the walls of which have an outer diameter such that they fit tightly against the inner wall of tube 12. The walls are thicker than is the bottom wall of the plug. The thick walls resist deformation, but the plug bottom, being less thick, deforms more readily under pressure. It responds like a diaphragm.

A central downwardly extending boss 88 is integrally formed on the bottom wall of the plug. A silver wire 90 extends through a hole which pierces the boss and the plug bottom. As in the other embodiments, the wire 90 is gripped by the resilient plug material. A silver-silver chloride body is scintered on the lower end of the silver wire. A central portion 92 of the wire, inside the plug 86, is bent to hairpin shape and the upper end extends through a central opening in a metal disc 94 and is soldered to the disc. The metal disc is disposed to lie in a plane parallel to the bottom wall of the plug 86 and perpendicular to the electrode axis. In this preferred form, the side walls of the disc 94 are tapered inwardly whereby the upper face of the disc has greater diameter than does the lower face. The upper rim of the plug 86 is complementally formed. The upper rim of the cup-shaped plug is tapered such that the rim surface extends upwardly and outwardly. The effect is to change the direction of force exerted by the cup rim on the tapered margin of the disc. Upward force on the plug face 84 is translated through the cup sides into a force against the disc edges that is translated into pressure of the cup walls against the tube walls. That enhances sealing effect and prevents leakage of electrolyte into the interior of the cup.

This design relies on diaphragm action at the cup bottom 84 to accommodate changes in electrolyte volume with temperature change. However, instead of using compression of an air cavity to provide return spring action, this unit employs a light compression spring 96 trapped between the bottom side of disc 94 and the upper side of the plug bottom wall 84. The wire section 92 is bent into hairpin or similar shape to provide an extra length of wire. That is a requirement because the separation of the disc and the plug or cup bottom 84 changes with electrolyte volume.

The center conductor of coaxial cable 98 is soldered to the upper face of disc 94 prior to insertion of the plug-spring-disc assembly into the tube 80. The assembly wire technique described above is employed to insure removal of all air from the electrolyte space. Using a probe, the disc 94 is held down against the force of spring 96 while a potting-sealing resin is introduced into the electrode body above the disc to form a sealing body 100. Later, when the sealing body 100 has become sufficiently hard so that the hold-down probe is not needed, the space occupied by the probe can be filled with a column of resin such as the column 102.

In this FIG. 4, as in the others, advantage is taken of the fact that the loop strength of glass is relatively great and the fact that the bulb to body junction can be made heavy and strong. As a consequence, a very considerable pressure can be applied to the electrolyte body. The stiffness of spring 96 can be selected whereby the range of internal pressure operation is greater in this design than what can be achieved with the arrangements shown in the other figures.

The sensor of FIG. 5 employs a plug 70 whose interior is only partly filled. An air filled hollow 110 is formed behind the lower wall 108 of the plug. The lower wall exhibits a diaphragm action. It deforms in response to increased pressure as an incident to increase in electrolyte volume. Deformation is opposed by the renitance of the lower wall 108 and by the pressure of the air in the cavity 110. The air in that cavity is compressed by wall deformation.

In the FIG. 5 design, the silver wire is bent to provide slack and is soldered to an electrical connector 102 in cavity 110. The hairpin bends are required because of change in the distance between the connector 102, whose position is fixed, and the diaphragm wall 108.

The banana plug connector 102 is engaged by the mating connector of an electronic, signal processing package 104. The design of the electronic package forms no part of the invention. Accordingly, it has been represented schematically. However, one of the advantages of the invention is that most of the space within electrode bodies of conventional size is unused and is available to house the electronic and other elements of a measuring system. The electrodes of FIGS. 4 and 5 have been shown in enlarged form for the sake of clarity, but even in actual size the bodies of these electrodes, and the electrode of FIGS. 1 and 2, can house temperature sensors, operational amplifiers, and other elements that are best mounted close to the liquid-to-metal junction.

Although we have shown and described certain specific embodiments of our invention, we are fully aware that many modifications thereof are possible. Our invention, therefore, is not to be restricted except insofar as is necessitated by the prior art.

We claim:
1. An electrode comprising:
    a container for electrolyte including a wall at which electro-chemical sensing is to be accomplished;
    a body of electrolyte disposed in said container overlying said wall;

maintaining means for maintaining said electrolyte in intimate contact with said wall against gravitational force in every spacial orientation of the electrode;

said maintaining means comprising a piston which is trapped between said container and said body of electrolyte to increase with temperature and which is biased to maintain intimate contact with said electrolyte to prevent formation of bubbles as the volume of electrolyte is decreased;

the piston being formed with two spaced, outwardly extending resilient encompassing flanges by which it engages the walls of the container and which yields to permit piston action by the central region of said piston.

2. An electrode comprising:

a container for electrolyte including a wall at which electro-chemical sensing is to be accomplished:

a body of electrolyte disposed in said container overlying said wall;

maintaining means for maintaining said electrolyte in intimate contact with said wall against gravitational force in every spacial orientation of the electrode;

said maintaining means comprising a structure which is trapped between said container and said body of electrolyte and which yields to permit the volume of said electrolyte to increase with temperature and which is biased to maintain intimate contact with said electrolyte to prevent formation of bubbles as the volume of electrolyte is decreased;

said maintaining means comprising a resilient portion and being trapped between the container and said body of electrolyte with said resilient portion in engagement with an inner surface of said container;

said resilient portion of said maintaining means being maintained in compression whereby to form a seal between said resilient portion and said inner surface against the passage of electrolyte;

said maintaining means including force increasing means for increasing the force with which said inner wall of the container is engaged by said resilient portion of said maintaining means; and said force increasing means including a body of gas and means for transferring heat to the gas upon the occasion of an increase in electrolyte temperature whereby to tend to increase one or both of the volume and pressure of said gas on the occasion of an increase in volume of said electrolyte.

3. An electrode comprising:

a container for electrolyte including a wall at which electro-chemical sensing is to be accomplished;

a body of electrolyte disposed in said container overlying said wall;

maintaining means for maintaining said electrolyte in intimate contact with said wall against gravitational force in every spacial orientation of the electrode;

said maintaining means comprising a structure which is trapped between said container and said body of electrolyte and which yields to permit the volume of said electrolyte to increase with temperature and which is biased to maintain intimate contact with said electrolyte to prevent formation of bubbles as the volume of electrolyte is decreased;

said container including a cylindrical portion;

said maintaining means being disposed in said cylindrical portion and forming a plug having an electrolyte engaging surface moveable as an incident to change in the volume of the electrolyte with temperature;

said plug spanning said cylindrical portion to form a seal against passage of electrolyte past said plug between the plug and the inner surface of the container;

said plug being effective to define a gas-filled void the pressure of which gas is variable with movement of said electrolyte engaging surface.

4. The invention defined in claim 3 in which said plug comprises a pair of spaced, outwardly extending flanges encompassing said plug and engaging spaced annular areas of the cylindrical inner wall of said container.

5. The invention defined in claim 4 in which the plug and its flanges and the inner wall of said container defining an annular cavity filled with gas.

6. The invention defined in claim 5 in which said plug is an effective conductor of heat to the gas in said annular cavity from the electrolyte whereby the temperature and the compression of gas in said cavity is increased as an incident to heating of said electrolyte.

7. The invention defined in claim 4 in which said flanges are formed of resilient material which yield from a first position in response to an increase of electrolyte volume and tend to be returned by their renitance to said first position in response to subsequent decrease in electrolyte volume.

8. The invention defined in claim 3 in which said plug is hollow.

9. The invention defined in claim 3 in which said plug comprises a piston.

* * * * *